(12) United States Patent
Pfanstiehl

(10) Patent No.: US 8,020,563 B2
(45) Date of Patent: Sep. 20, 2011

(54) ULTRA THIN EAR PLUGS

(76) Inventor: John Pfanstiehl, Indian Rocks Beach, FL (US)

( * ) Notice: Subject to any disclaimer, the term of this patent is extended or adjusted under 35 U.S.C. 154(b) by 388 days.

(21) Appl. No.: 11/957,760

(22) Filed: Dec. 17, 2007

(65) Prior Publication Data

US 2009/0151735 A1    Jun. 18, 2009

(51) Int. Cl.
  *A61F 11/00* (2006.01)
  *H04R 25/00* (2006.01)
  *H04R 25/02* (2006.01)
  *A61B 7/02* (2006.01)

(52) U.S. Cl. ......... 128/864; 181/129; 181/130; 181/135

(58) Field of Classification Search .................. 128/864, 128/865, 866–868; 181/129, 130, 135, 134; 264/467, 464, 466; 206/205, 570, 581, 339, 206/438, 440, 441; 381/312, 317, 322, 324
See application file for complete search history.

(56) References Cited

U.S. PATENT DOCUMENTS

| | | | |
|---|---|---|---|
| 4,053,051 A | 10/1977 | Brinkhoff | |
| 4,253,452 A | 3/1981 | Powers et al. | |
| 4,344,425 A | 8/1982 | Strauss | |
| 4,434,794 A | 3/1984 | Leight | |
| 4,498,469 A | 2/1985 | Csiki | |
| 4,702,238 A | 10/1987 | Scott | |
| 5,119,833 A | 6/1992 | Powers | |
| 5,153,387 A | 10/1992 | Zwislocki et al. | |
| 5,452,731 A | 9/1995 | Dickman | |
| 5,819,745 A | 10/1998 | Mobley et al. | |
| 5,853,247 A * | 12/1998 | Shroyer | 383/95 |
| 5,957,136 A | 9/1999 | Magidson et al. | |
| 5,996,584 A * | 12/1999 | Oliveira et al. | 128/864 |
| 6,105,715 A * | 8/2000 | Knauer | 181/135 |
| 6,138,790 A | 10/2000 | Leight | |
| 6,427,800 B1 | 8/2002 | Hiselius et al. | |
| 6,568,395 B2 * | 5/2003 | Tiemens | 128/864 |
| 6,761,173 B1 | 7/2004 | Kuno et al. | |
| 7,022,890 B2 * | 4/2006 | Sessions | 602/46 |
| 2004/0079579 A1 * | 4/2004 | Barwacz | 181/135 |
| 2007/0074991 A1 * | 4/2007 | Heisserer | 206/438 |

* cited by examiner

*Primary Examiner* — Patricia Bianco
*Assistant Examiner* — Ophelia Hawthorne

(57) ABSTRACT

An ultra thin ear plug enables sound protection to be conveniently carried inside a wallet. The ear plug is made of a slow-recovery thin foam strip. The user rolls the strip into a cylinder, compresses the cylinder and inserts the compressed foam cylinder into the ear canal. The foam strip can incorporate a pressure sensitive adhesive on one surface so that the ear plug retains the cylindrical shape after being rolled up. Tapered ends can assist sealing by minimizing the existence of an air gap at the center of the cylinder and on the ear canal. A flexible envelope about 0.008 inch thick and of credit card dimensions can provide packaging for two or more ear plugs and can provide a large surface area for promotional advertising. Total thickness of the packaged ear plugs can be thinner than 0.050 inch or the thickness of a credit card.

21 Claims, 5 Drawing Sheets

ROLL THIS SIDE UP

ULTRA THIN EAR PLUGS

FIELD OF THE INVENTION

The present invention relates to ear plugs for reducing sound levels.

BACKGROUND OF THE INVENTION

The many needs for protection of the human ear have spawned numerous inventions for specific purposes. However none of the prior art discloses ear plugs that can easily fit into a wallet.

U.S. Pat. No. 6,568,395 to Tiemens (2003) discloses a multiple ear plug arrangement that cuts an extrusion into a chain of at least ten ear plugs. The purpose is to enable low cost manufacture and storage of ear plugs and convenient dispensing of individual ear plugs. The chain of ear plugs is stored in a plurality of loops in a container. The extrusion can include a stiffening core.

U.S. Pat. No. 6,761,173 to Kuno, et al. (2004) discloses a vented ear plug with a communicating passage or vent for decreasing the pressure difference between the inside of the external auditory canal and the external atmosphere.

U.S. Pat. No. 6,761,173 to Hiselius, et al. (2004) discloses a sound-attenuating ear plug, with foil which is rounded in the longitudinal direction and which is extended transversely of this longitudinal direction and is responsible for the major part of the sound-attenuating effect. The invention also relates to a method of manufacturing such an ear plug.

U.S. Pat. No. 5,996,584 to Oliveira, et al. (1999) discloses a reusable ear plug, formed from a core, about which is adhered a strip of slow recovery foam. After each use of the device, the strip of foam is generally removed and discarded; typically, a new strip is applied the next time the device is used.

U.S. Pat. No. 5,957,136 to Magidson, et al. (1999) discloses a hollow ear plug with an insertion member.

U.S. Pat. No. 5,819,745 to Mobley, et al. (1998) discloses a pressure regulating ear plug for regulating the rate of change of pressure inside an ear. Disposed within the ear plug is a pressure regulator with a slow leak rate. The pressure regulator is preferably made of a porous ceramic material.

U.S. Pat. No. 5,452,731 to Dickman (1995) discloses a flexible, disposable ear plug which is capable of decreasing humidity levels from the environment within the inner ear of a user. The ear plug includes a resilient hygroscopic body and a removable integral tip which are both surrounded by a flexible water-proof casing. When the integral tip is removed from the body of the ear plug, a surface of the hygroscopic body of the ear plug is exposed.

U.S. Pat. No. 5,153,387 to Zwislocki, et al. (1992) discloses a layered ear plug made of a stack of thin flexible plastic discs bonded together about a central hole and loose at the edges. The purpose is to permit easy insertion and removal from the ear.

U.S. Pat. No. 4,702,238 to Scott (1987) discloses an ear plug for attenuating sound and providing a watertight seal. It is made of closed cell foam to provide a multitude of convex and concave surfaces to reflect, dissipate and attenuate sound waves.

U.S. Pat. No. 4,498,469 to Csiki (1985) discloses an ear plug made of an elastic material enveloped by a deep-drawn sheath of thin flexible plastic film and a stiffer collar or flange. Production of the ear plug includes deep-drawing a thermoplastic film or foil into a sheath and filling the sheath with elastic material.

U.S. Pat. No. 4,434,794 to Leight (1984) discloses an ear plug with a shell formed of closed cell foam material. The shell surface has a multiplicity of small bumps to avoid wrinkling when the shell is squeezed into the ear canal. A stem of resilient material lies freely moveable in the shell, and is short so it extends substantially no further than the open end of the shell.

U.S. Pat. No. 4,344,425 to Strauss (1982) discloses an ear plug with a tacky adhesive surface to help attach the plug in place. Retention of the plug does not rely on friction developed by compression of the body of the plug as it is inserted in the ear canal, and therefore the plug need not fit tightly into the ear canal. In some cases the plug may merely overlie the mouth of the canal. The adhesive surface may be a layer of adhesive applied to a substrate or it may be the surface of a body of plug material which is inherently tacky.

U.S. Pat. No. 4,053,051 to Brinkhoff (1977) discloses a thin sound-attenuating mat of fibers, which forms an earplug that is removable with an inserter from a container to permit insertion of the earplug in an ear by means of the inserter, which is then withdrawn from the plug. The earplug is made by placing a flat fibrous mat against the open end of the container and then pushing it into the container by means of the inserter stem.

U.S. Pat. No. 6,138,790 to Leight (2000) discloses a noise blocking ear plug which has a band with outer portions that are bent to prevent the ear-engaging pods from touching the ground, whether placed right-side-up or upside-down on the ground.

U.S. Pat. No. 5,119,833 to Powers (20) discloses a compressible ear plug that has a cross-section formed by a plurality of three or four sides wherein there is an angle no greater than 90.degree between at least two sets of adjoining sides. In this manner, the plug can be cut from a sheet of material with virtually no waste resulting.

U.S. Pat. No. 4,253,452 to Powers, et al. (1992) discloses an ear plug assembly made of a pair of plug bodies made from open cell resilient foam material having a slow recovery rate. These are interconnected by a flexible cord having its free ends inserted into preformed holes in the plug bodies before the holes close under the influence of the recovery rate.

The above listed prior art is intended to solve specific needs not related to enabling a very thin ear plug. The following application discloses a multiple-component package that attempts to compress conventional ear plugs and hold them in a compressed state that is suitable for carrying in a wallet, but falls significantly short of that goal.

U.S. provisional patent application 20070074991 by Heisserer (2007) discloses an ear plug package whose purpose is to compressibly and compactly store one or more ear plugs. The ear plug package comprises a base, a body, and a retaining seal. The base is coupled to the body, and the body includes one or more compartments, each adapted to receive and store at least one compressible ear plug. The retaining seal is removable, and may comprise multiple sections, with perforations between sections.

The multiple components increase the cost and complexity of materials and manufacturing. In addition, the bulges on one or more surfaces from the compressed ear plugs or from a vacuum interfere with reading indicia printed on those surfaces. Furthermore, the bulges on the printing surface make it difficult and more costly to custom print indicia after packaging the enclosed ear plugs. If material is used that is sufficiently rigid to compress the ear plugs without forming bulges, the thickness of the package is significantly increased.

The total thickness of the package is a critical shortcoming. The disclosed package can have three layers: a "sturdy, durable" base, a body at least equal in thickness as the practically compressed thickness of a standard ear plug (typically about 0.500 or 13 mm), and a seal layer that is sufficiently sturdy to not bulge too much or have "a deflection of 2.0 mm or less." Adding the high end of the range of thickness disclosed for the layers results in a package that is 13 mm or over ½ inch thick. The application also says "The overall thickness of (the) package is preferably 8.0 mm or less." Even if 7 mm was achieved in production, that is still over ¼ inch thick and almost six times as thick as a credit card. Most people would prefer not to stuff an additional item that is over ¼ inch thick into their wallets.

SUMMARY OF THE INVENTION

The object of present invention is an ear plug that is so thin that users will readily accept its inclusion in their wallet, pocket or other areas where a very thin package is desirable. The objects and advantages of the present invention include the following:

a) Ear plugs that are as thin as a credit card and therefore can be desirably carried in a wallet or easily stored in a glove compartment, purse or pocket.

b) Ear plugs that are inexpensive to manufacture.

c) Ear plugs that fit in a container or envelope that has a surface area size similar to two sides of a business card for advertising or promotion of a product, event, company or service.

d) Ear plugs that can be packaged in a container or envelope that is flat, thin and flexible and therefore can be very inexpensively imprinted.

e) Ear plugs that can be packaged in a container or envelope that is ver inexpensively manufactured.

f) Ear plugs that do not require being compressed to be packaged in a very thin container.

g) Ear plugs that do not require a vacuum to be packaged in a very thin container.

h) Ear plugs that will not expand if the packaging container is punctured or its seal fails.

i) Ear plugs that will not expand if the packaging container is opened.

j) Ear plugs that can easily be returned to a very thin container after use.

k) Ear plugs that do not cause bulges or deflections when packaged in a container that interferes with reading indicia printed upon the packaging surface.

l) Ear plugs that do not cause bulges or deflections in packaging when packaged in a container that makes custom imprinting of indicia upon the packaging surface more costly and time consuming.

m) Ear plugs that provide a large flat area for indicia that is inexpensive to imprint and easy to read.

n) Ear plugs that provide a large area for indicia that will not contact the user's skin thereby preventing ink transfer.

These and other important objects, features, and advantages of the invention will become apparent as this description proceeds.

The need for ear plugs that attenuate loud sounds is well known. It is also well accepted as shown by the very large size of the market. In addition to providing a comfortable sound level and protecting the hearing of the user, the ear protection ear plugs provide is often required by safety regulations. However, a major problem is that high sound levels are often encountered by individuals at times or in locations where the need for ear protection was not planned. Conventional ear plugs are rarely carried on a person due to their awkward size. The present invention solves this problem and provides additional advantages.

The present invention discloses ear plugs made from very thin strips of slow-recovery foam. The user rolls a foam strip into a cylinder that is similar in dimensions and shape to a standard foam ear plug. The user then compresses the cylinder and inserts the compressed foam cylinder into the ear canal in the same process as a standard ear plug. Making the earplugs in a very thin strip of foam enables them to be carried or stored in a much more compact form than standard ear plugs.

A thin envelope about the same thickness as a standard letter envelope but of credit card dimensions can provide packaging for two or more ear plugs and can provide a large surface area for promotional advertising. Total thickness of the packaged ear plugs can be thinner than 0.050 inch or the thickness of a credit card. This enables ear plugs to be carried in a wallet, a purse or a small pocket as easily and conveniently as a credit card.

The foam strip can incorporate a pressure sensitive adhesive on one surface so that the ear plug retains the cylindrical shape after being rolled up. Tapered ends can assist sealing by minimizing the existence of an air gap at the center of the rolled cylinder and on the end that presses against the ear canal. The ear plugs of the present invention can also be stored or distributed on a roll.

Additionally, the ear plugs of the present invention are inexpensive to produce, inexpensive to manufacture and provide excellent large flat surfaces for advertising and promotion that can be printed either before or after the ear plugs are packaged.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DETAILED DESCRIPTION OF EXEMPLARY EMBODIMENTS OF THE INVENTION

Figure 1:
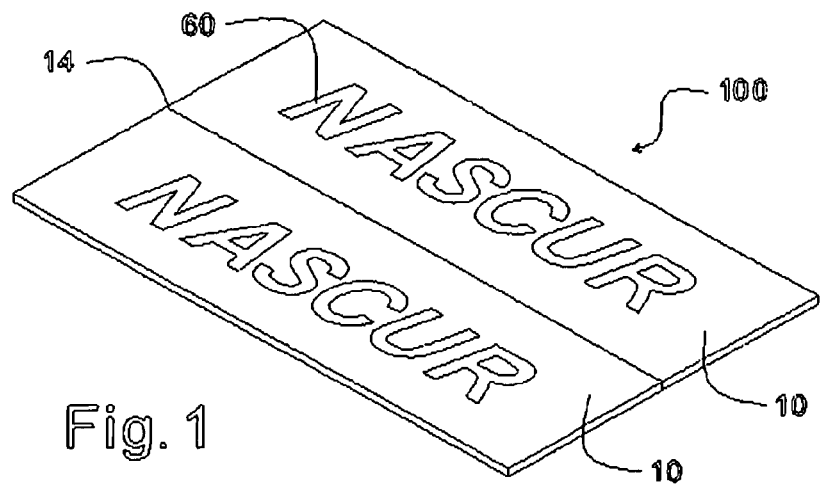
FIG. 1 is a perspective view of two ear plug strips of the present invention.

FIG. 1 shows a preferred embodiment of the ultra thin ear plugs of the present invention. Two ear plug strips (10) form a strip collection (100) that is approximately the same length and width as a credit card or business card. Strip serrated edges (14) can be made by die cutting or other production means to cut the strips from an inexpensive strip of flat slow-recovery foam. The two strips can be 1.000 inch wide by 3.200 long to allow them to fit inside a credit card size envelope, about 2.120 inches by 3.360 inches. At a thickness of 0.047, the strip will roll up to produce a 0.438 inch (7/16 inch) diameter cylinder, similar in dimensions to standard ear plugs. The serrated edges enable the strips to be easily handled and packaged as a collection of two or more and allow the strips to be separated when needed. For added convenience, two strips can be rolled up at the same time and then separated after they form a cylinder.

The strip form of the ear plugs of the present invention provides substantially more visible surface than standard ear plugs for imprinting indicia (60) directly on the ear plug. Additionally, and unlike conventional ear plugs, the indicia can be on the internal surface of the ear plug when it is rolled into a cylinder thereby preventing any transfer of ink from the ear plug to the user's skin.

Figure 2:
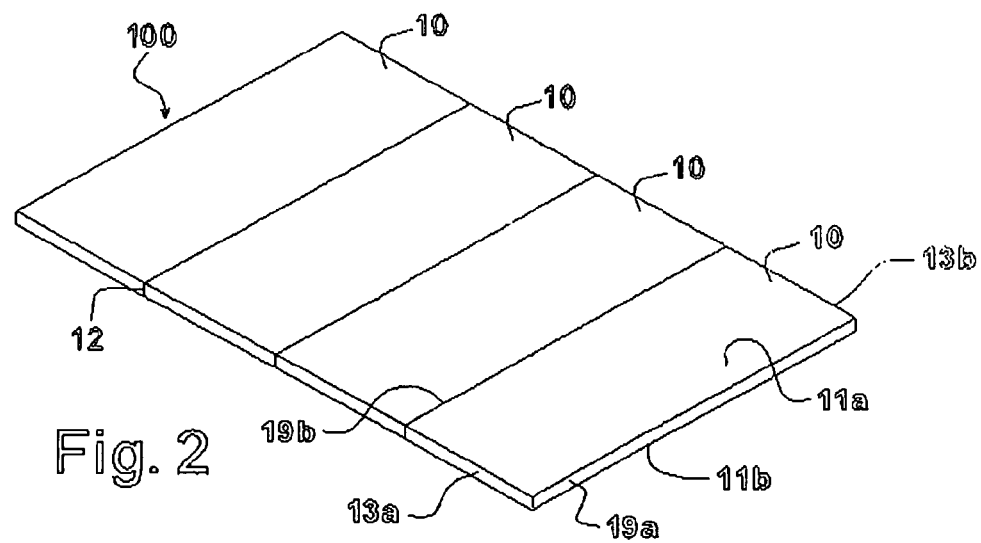
FIG. 2 is a perspective view of four ear plug strips of the present invention.

FIG. 2 shows another embodiment of the ultra thin ear plugs of the present invention for reducing sound level which includes strips of slow recovery foam material having a first planar surface (11a), a second planar surface (11b) substantially parallel to the first planar surface (11a), a first side surface (19a) generally perpendicular to one of the planar surfaces (11a and 11b), a second side surface (19b) opposite the first side surface (19a), a first end surface (13a) generally perpendicular to one of the planar surfaces (11a and 11b), and a second end surface (13b) opposite the first end surface (13a). Four ear plug strips (10) form a strip collection (100) that is approximately the same length and width as a credit card or business card. Strip cut edges (12) can be made by die cutting or other production means to cut the strips from an inexpensive strip of flat slow-recovery foam. The four strips can be 0.800 inch wide by 2.000 inches long to allow them to fit inside a credit card size envelope, about 2.120 inches by 3.360 inches. At a thickness of 0.075 inch, the strip will roll up to produce a 0.438 inch (7/16 inch) diameter cylinder, similar in dimensions to standard ear plugs. When the strips are stored in a wallet, typically there is some pressure exerted against them further reducing the thickness of the strips.

Figure 3:
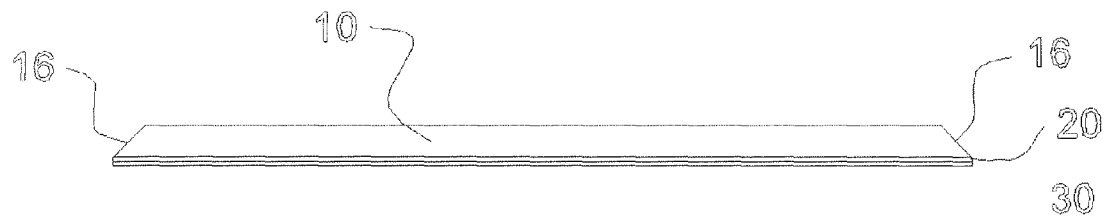
FIG. 3 is a side elevational view of another embodiment of an ear plug strip of the present invention.

FIG. 3 shows a side view of another embodiment of the ultra thin ear plugs of the present invention. Adhesive (20) is on one side of strip (10) and is covered by adhesive tear-off backing (30). The tear-off backing is removed and the foam strip is rolled with the adhesive side in. The adhesive prevents the foam strip from unrolling. The strip thereby remains in the cylindrical shape. Strip beveled end (16) can prevent small air gaps at the internal end or the external end of the strip when it is rolled into a cylinder.

Figure 4:
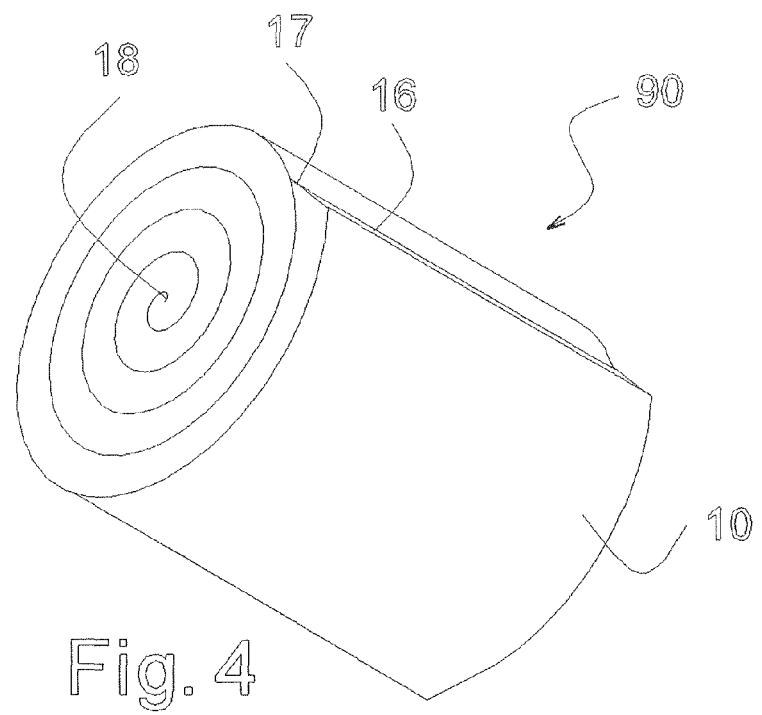
FIG. 4 is a perspective view of an ear plug strip of FIG. 3 of the present invention rolled into a cylinder.

FIG. 4 shows a perspective view of the ear plug of the present invention when it is rolled into a substantially solid cylindrical shape (90). Strip beveled end (16) facilitates sealing of the external end of the strip (17) when the cylindrical shape is placed in the ear canal. The beveled end also facilitates sealing of the internal end of the strip (18) when it is rolled into a cylinder. In another embodiment, shown in FIG. 6a through FIG. 6d, adhesive (20) is located on a portion of one side of the strip abutting the external end (17) in the same fashion as adhesive is located on a cigarette rolling paper.

Figure 5A:
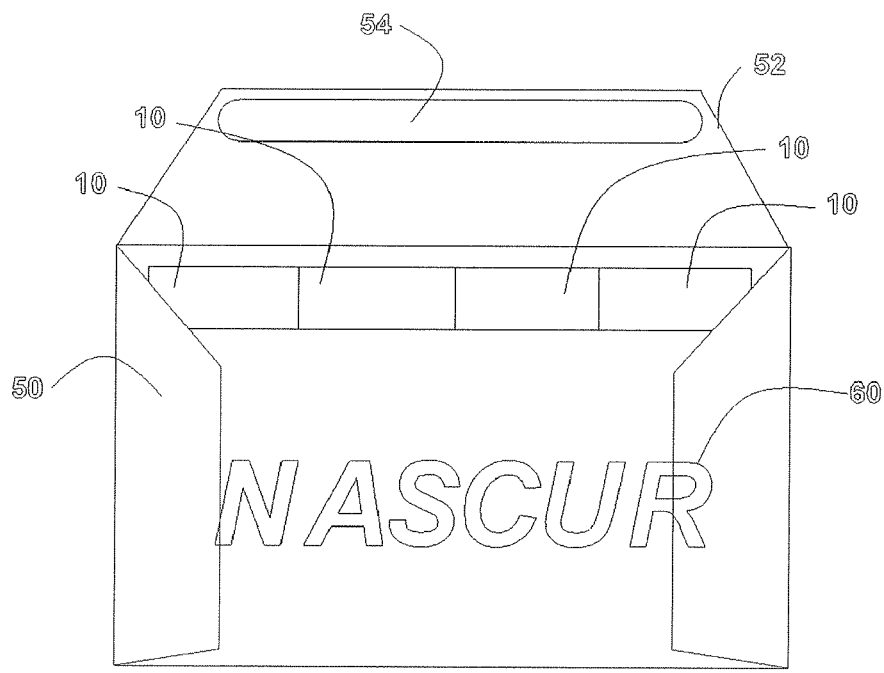
FIG. 5a is a top elevational view of ear plug strips of the present invention packaged in an envelope.

FIG. 5a shows a top view of another embodiment of the ultra thin ear plugs of the present invention. Ear plug strips (10) are packaged in an envelope (50). Because the ear plug strips do not have to be compressed, the envelope can be manufactured very inexpensively of paper or other materials obvious to those skilled in the art. Envelope cost can be less than $0.02 in quantity. Paper used for making an envelope is typically 0.004 inch thick resulting in an envelope thickness of about 0.008 inches. Other envelope materials such as foil or cellophane can be as thin as 0.001 and thereby resulting in a total thickness of a package containing the ear plug of FIG. 1 of 0.049 inches.

Both front and rear surfaces of the envelope provide large areas for indicia (60) for advertising or promotion of a product, event, company or service. Because the envelope packaging is flat, thin and flexible, it can be very inexpensively imprinted. Because the ear plugs are flat strips when packaged, they do not cause bulges or deflections that interfere with reading indicia printed upon the packaging surface. Furthermore, the thin flexible packaging that has substantially flat surfaces without multiple bulges enables custom imprinting of indicia after packaging of the ear plugs of the present invention by common printing processes that are fast and inexpensive.

Figure 5B:
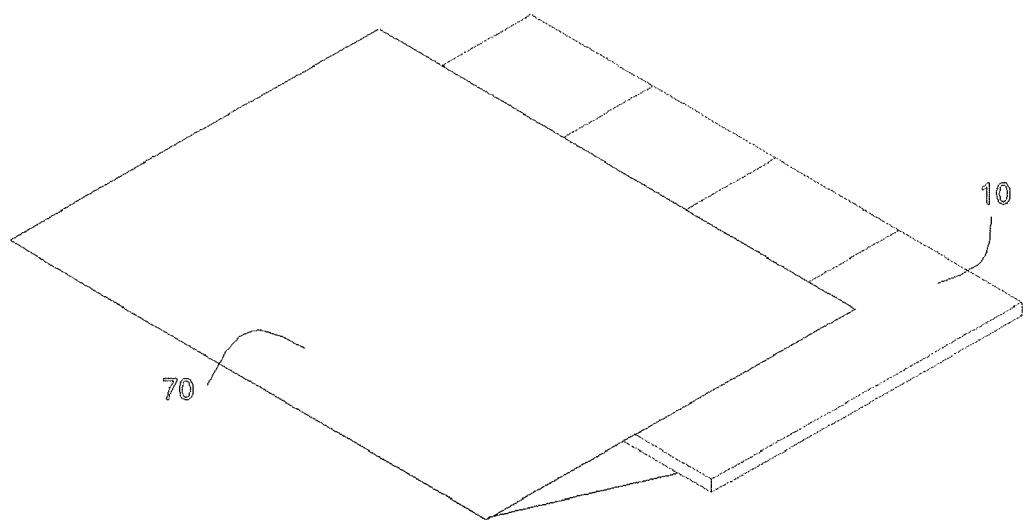
FIG. 5b is a perspective view of ear plug strips of the present invention inserted in a sheath.

Ear plugs of the preferred embodiment can easily be returned to the envelope after use and thereby continue to be carried in a very thin container. The packaging envelope can have glue (54) on flap (52) to seal the package. The envelope also can have four flaps on one surface to permit that side to be fully opened so that the foam strips do not have to be slid along the interior surfaces of the envelope during removal or when they are placed back into the envelope. FIG. 5b shows an alternative method where the ear plug strips (10) are inserted in a folded sheath (70) made of thin paper or foil to reduce friction and thereby facilitate insertion and removal into the envelope, similar to wrapping sticks of chewing gum. Packaging for the ear plug strips can also be a flat plastic bag such as a small zip-lock bag. A transparent plastic bag enables a very inexpensive paper product such as a business card to carry the indicia and be inserted between the ear plug strips and the bag. Credit card size zip-lock style bags can be reclosed and resealed and cost less than $0.03 in quantity. Hanger holes and other packaging features obvious to those skilled in the art can also be included.

Figure 6A:
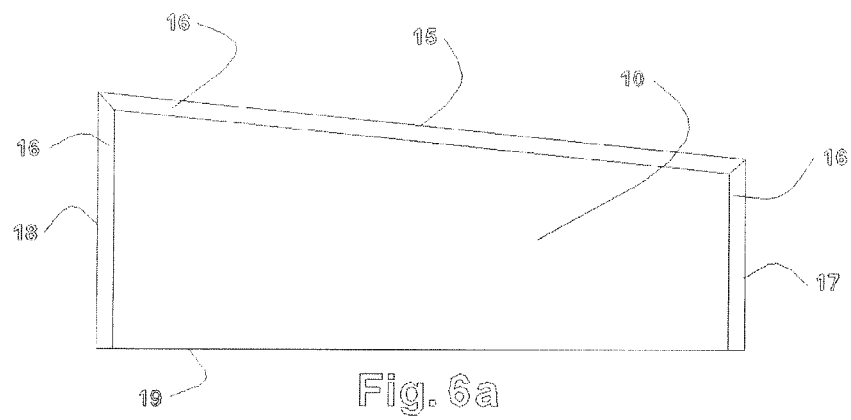
FIG. 6a is a top elevational view of an ear plug strip of the present invention.
Figure 6B:
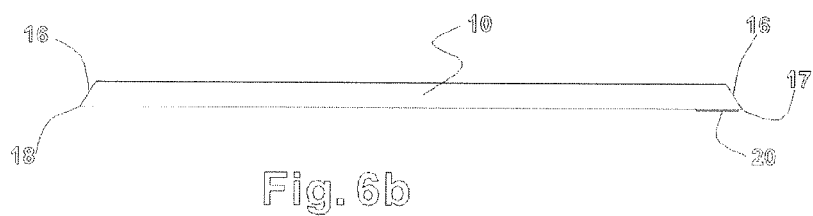
FIG. 6b a side elevational view of an ear plug strip of the present invention.
Figure 6C:
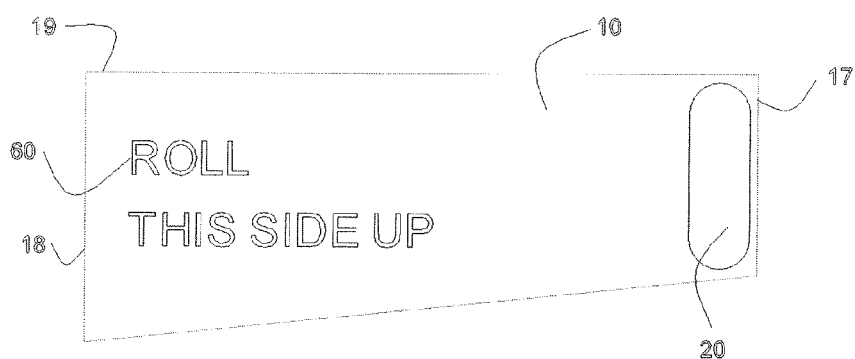
FIG. 6c a bottom elevational view of an ear plug strip of the present invention.
Figure 6D:
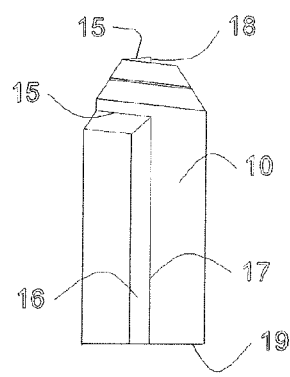
FIG. 6d is a top elevational view of the strip rolled into a cylinder.
Figure 7A:
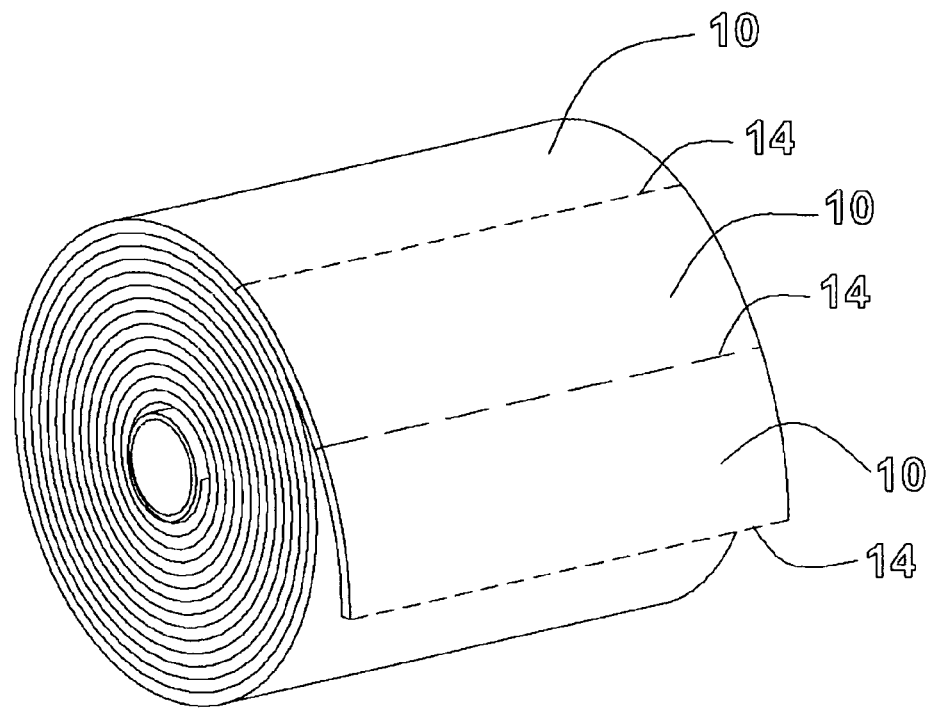
FIG. 7a is a perspective view of the rolled collection of strips without tear off backing cover of the present invention described in Claim 16.
Figure 7B:
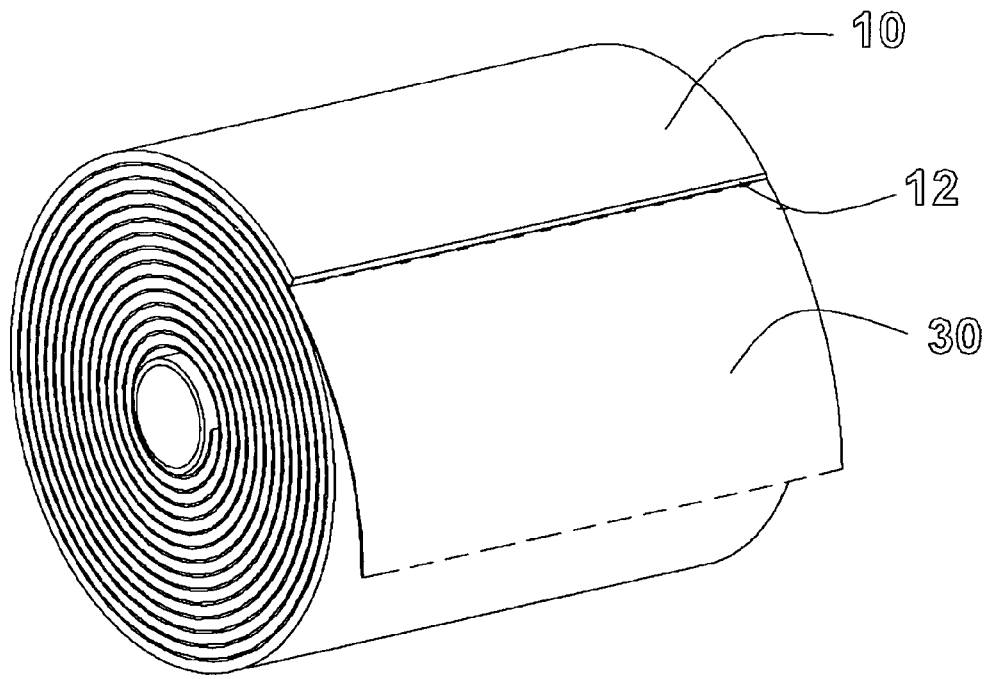
FIG. 7b is a perspective view of the rolled collection of strips with tear off backing cover of the present invention described in Claim 17.

FIG. 6a shows a top view of another embodiment of the ultra thin ear plugs of the present invention. Ear plug strip (10) is cut tapered so that external end (17) is slightly shorter than internal end (18). Rolling the ear plug strip while keeping the square side (19) square creates a cylinder with one end that is partially cone-shaped, as shown in FIG. 6d. This facilitates insertion of the ear plug into an ear canal. A strip beveled end (16) can be on angled side (15) to create a cone that has no sharp right angle edges and therefore further facilitate insertion of the ear plug into an ear canal. FIG. 6b illustrates that adhesive (20) can be on what becomes the inside surface of the strip adjacent to the external end to hold the ear plug in the cylindrical shape after it is rolled up. FIG. 6c illustrates that indicia (60) can be printed on one side of the ear plug to provide instructions or advertising. A cone-shaped end can also be created by other non-rectangular shapes including triangles and ovals.

This invention is clearly new and useful. The present invention overcomes all the primary disadvantages of the prior art devices and methods. Moreover, it was not obvious to those of ordinary skill in this art in view of the previous prior art.

The invention comprises the features of construction, combination of element and arrangement of parts that will be exemplified in the construction hereinafter set forth, and the scope of the invention will be indicated in the claims.

It will thus be seen that the objects set forth above, and those made apparent from the foregoing description, are efficiently attended. Although the present invention has been described with reference to particular embodiments, one skilled in the art will recognize that changes may be made in form and detail without departing from the spirit and scope of the invention. Therefore, all matters contained in the foregoing construction or shown in the accompanying drawings should be considered in all respects as illustrative and not restrictive.

It is also understood that the following claims are intended to cover all of the generic and specific features of the invention herein described, and all statements of the scope of the invention which, as a matter of language, might be said to fall there between.

What is claimed is:

1. An ear plug for reducing sound level comprising:
    a first strip of slow recovery foam material having
        a first planar surface;
        a second planar surface substantially parallel to said first planar surface;
        a first side surface generally perpendicular to one of said planar surfaces;
        a second side surface opposite said first side surface;
        a first end surface generally perpendicular to one of said planar surfaces;
        a second end surface opposite said first end surface;
    a second strip of slow recovery foam material having
        a first planar surface;
        a second planar surface substantially parallel to said first planar surface;
        a first side surface generally perpendicular to one of said planar surfaces;
        a second side surface opposite said first side surface;
        a first end surface generally perpendicular to one of said planar surfaces; and
        a second end surface opposite said first end surface, wherein one of the side surfaces of said second strip substantially adjoins one of the side surfaces of said first strip, whereby the strips are separated and the strip is rolled upon itself into a substantially solid cylinder.

2. The ear plug of claim 1, further including:
    an envelope for packaging at least two of said strips of slow recovery foam material.

3. The ear plug of claim 2, wherein a size of said envelope is selected from the group comprised of credit card size and business card size.

4. The ear plug of claim 2, further including a folded planar sheath to encase said strips of slow recovery foam material whereby friction is minimized during insertion and removal from said envelope.

5. The ear plug of claim 2, wherein said envelope has one planar surface that opens completely whereby said strips of slow recovery foam material are removed without sliding said foam over said envelope.

6. The ear plug of claim 2, wherein said envelope is made from a material selected form the group of paper, foil and plastic.

7. The ear plug of claim 2, wherein said envelope further includes indicia on at least one planar surface of said envelope.

8. The ear plug of claim 2, wherein said envelope is a flat plastic bag.

9. The ear plug of claim 8, wherein said flat plastic bag is transparent and further includes:
    a card wherein said card fits within said flat plastic bag; and
    printed indicia on said card.

10. The ear plug of claim 8, wherein said flat plastic bag is recloseable.

11. The ear plug of claim 1, further including:
    an adhesive on one of said planar surfaces; and
    a tear-off backing covering said adhesive.

12. The ear plug of claim 11, wherein said strip is joined to a plurality of said strips by a serrated cut in said tear off backing cover to form a strip collection whereby said strips are conveniently packaged in said strip collection selected from the group consisting of a collection of two of said strips, a collection of four of said strips, a flat collection of more than four of said strips and a rolled collection of more than four of said strips.

13. The ear plug of claim 1, wherein one or more of said side surfaces or said end surfaces are beveled.

14. The ear plug of claim 1, further including indicia on at least one planar surface.

15. The ear plug of claim 1, wherein said first end is longer than said second end, whereby when said strip is rolled into the substantially solid cylinder, at least one end of said substantially solid cylinder has a cone shaped profile to aid insertion into an ear canal.

16. The ear plug of claim 1, wherein said second planar surface is less than 0.150 inch from said first planar surface, said side surfaces are less than 3 inches in length and said end surfaces are less than 1.5 inches in length, whereby said first end surface is rolled so that said strip forms a substantially solid cylinder having a length less than 1.5 inches and a diameter less than one inch.

17. The ear plug of claim 1, wherein said strip is joined to a plurality of said strips by a serrated cut in said sides forming a strip collection whereby said strips are conveniently packaged in said strip collection selected from the group consisting of a collection of two of said strips, a collection of four of said strips, a flat collection of more than four of said strips and a rolled collection of more than four of said strips.

18. An ear plug for reducing sound level comprising:
    a strip of slow recovery foam material having a first planar surface;
    a second planar surface substantially parallel to said first planar surface;
    a first side surface generally perpendicular to said first planar surfaces;
    a second side surface opposite said first side surface;
    a first end surface generally perpendicular to said first planar surfaces;
    a second end surface opposite said first end surface; and
    an envelope having a front surface for packaging at least one of said strips of slow recovery foam material, wherein said envelope is substantially flat and wherein said front surface of said envelope is substantially parallel to said first planar surface of said strip of slow recovery foam material when said strip of slow recovery foam material is packaged within said envelope, whereby said front surface of said envelope remains substantially flat when said slow recovery foam material is packaged within said envelope whereby said strip is removed from said envelope and is rolled upon itself into a solid cylinder.

19. The ear plug of claim 18, further including:
    an adhesive on said first planar surface and
    a tear-off backing covering said adhesive wherein said tear-off backing is removed, said strip of slow recovery foam material is rolled upon itself to form a solid cylinder and said adhesive on said first planar surface abuts and adheres to said second planar surface whereby said strip of slow recovery foam material is prevented from unrolling from said solid cylinder.

20. A method of reducing sound level comprising the steps of:
 a) providing a first thin strip of slow-recovery foam having a first planar surface, a second planar surface substantially parallel to said first planar surface, a first side surface generally perpendicular to said first planar surfaces, a second side surface opposite said first side surface, a first end surface generally perpendicular to said first planar surfaces, and a second end surface opposite said first end surface;
 b) rolling said first thin strip of slow-recovery foam upon itself into a solid cylinder;
 c) compressing said solid cylinder into a compressed cylinder by rolling said solid cylinder between a thumb and at least one finger;
 d) inserting said compressed cylinder into a first ear canal wherein said compressed cylinder will expand and seal against the inner diameter of said first ear canal and thereby attenuate sound passing through said first ear canal;
 e) providing a second thin strip of slow-recovery foam having a first planar surface, a second planar surface substantially parallel to said first planar surface, a first side surface generally perpendicular to said first planar surface, a second side surface opposite said first side surface, a first end surface generally perpendicular to said first planar surface, and a second end surface opposite said first end surface;
 f) rolling said second thin strip of slow-recovery foam upon itself into a solid cylinder;
 g) compressing said solid cylinder into a compressed cylinder by rolling said solid cylinder between a thumb and at least one finger; and
 h) inserting said compressed cylinder into a second ear canal wherein said compressed cylinder will expand and seal against the inner diameter of said second ear canal and thereby attenuate sound passing through said second ear canal.

21. The method of claim 20 and further comprising the steps of:
 a) providing said first thin strip of slow-recovery foam with an adhesive on said first planar surface;
 b) providing a tear-off backing covering said adhesive;
 c) prior to rolling into said solid cylinder, removing and discarding said tear-off backing covering said adhesive; and
 d) prior to rolling into said solid cylinder, orienting said first thin strip of slow-recovery foam so that said adhesive will be on the internal surface of said solid cylinder, wherein said adhesive on said first planar surface abuts and adheres to said second planar surface whereby said first thin strip of slow recovery foam material is prevented from unrolling from said solid cylinder.

* * * * *